US00PP33889P2

(12) United States Plant Patent
Korlipara

(10) Patent No.: US PP33,889 P2
(45) Date of Patent: Jan. 18, 2022

(54) ***ECHINACEA* PLANT NAMED 'MOAB SUNSET'**

(50) Latin Name: ***Echinacea* spp.**
Varietal Denomination: Moab Sunset

(71) Applicant: Terra Nova Nurseries, Inc., Canby, OR (US)

(72) Inventor: Harini Korlipara, Tualatin, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 17/358,064

(22) Filed: Jun. 25, 2021

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 6/1448
See application file for complete search history.

*Primary Examiner* — Anne Marie Grunberg
(74) *Attorney, Agent, or Firm* — The Webb Law Firm

(57) ABSTRACT

A new and distinct variety of *Echinacea* plant characterized by enlarged disc florets forming an anemone-type inflorescence, strong orange ray florets and orange disc florets, ray florets which are mostly held horizontally to drooping, a short, upright habit with excellent color retention, and excellent vigor.

2 Drawing Sheets

Botanical classification: *Echinacea* spp.
Varietal denomination: 'Moab Sunset'.

BACKGROUND OF THE INVENTION

The present invention comprises a new and distinct cultivar of *Echinacea* plant having the varietal name 'Moab Sunset'. The new variety was discovered in Canby, Oreg. as the result of a planned breeding program for a landscape series with the purposes of providing *Echinacea* plants with compact habits and profuse, double inflorescences. The exact parents of 'Moab Sunset' are unknown, unnamed, unpatented, and proprietary interspecilk hybrids bred from *Echinacea paradoxa, Echinacea purpurea*, and *Echinacea tennesseensis*.

When 'Moab Sunset' is compared to *Echinacea* spp. variety named 'TNECHCMY' (U.S. Plant Pat. No. 31,142), 'Moab Sunset' exhibits a more upright growth habit. Further, the following characteristics distinguish 'Moab Sunset' when generally compared to other *Echinacea* varieties known to the breeder:

- Enlarged disc florets forming an anemone-type inflorescence;
- Medium orange ray florets and orange-red with orange disc florets;
- Ray florets which are mostly held horizontally to drooping;
- A short, upright habit with excellent color retention; and
- Excellent vigor.

The new variety has been asexually reproduced in Canby, Oreg. and has been found to retain its distinctive characteristics and remain true to type through successive asexual propagations. Propagation was conducted in tissue culture using standard micropropagation techniques by dividing terminal and lateral shoats. Each of the progeny exhibits identical characteristics to the original plant. The present invention has not been evaluated under all possible environmental conditions. The phenotype may vary with variations in environment without a change in the genotype of the plant.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
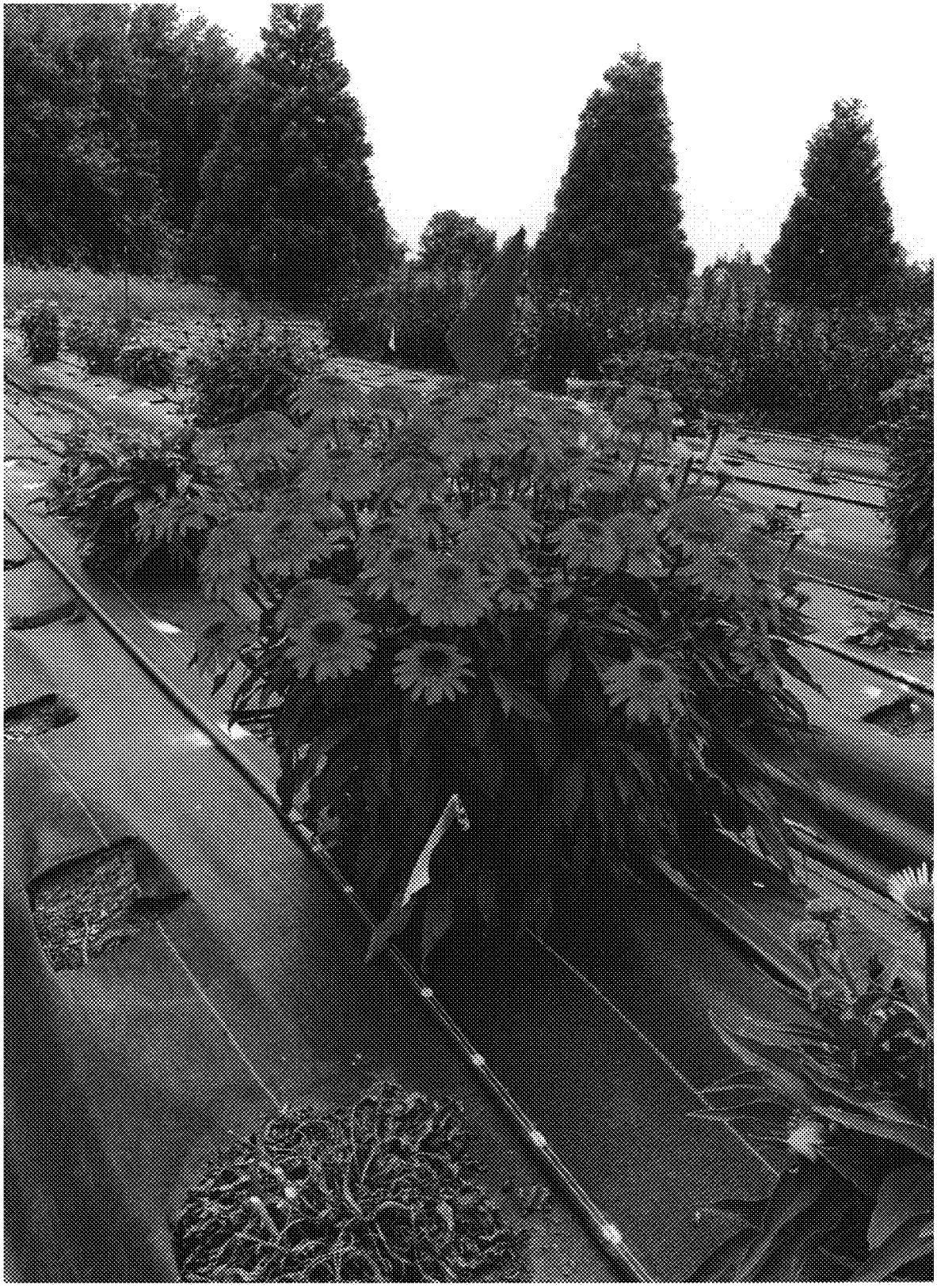
FIG. 1 shows a 17-month old plant of the new variety growing in the trial field in full sunset in early July in Canby, Oreg.
Figure 2:
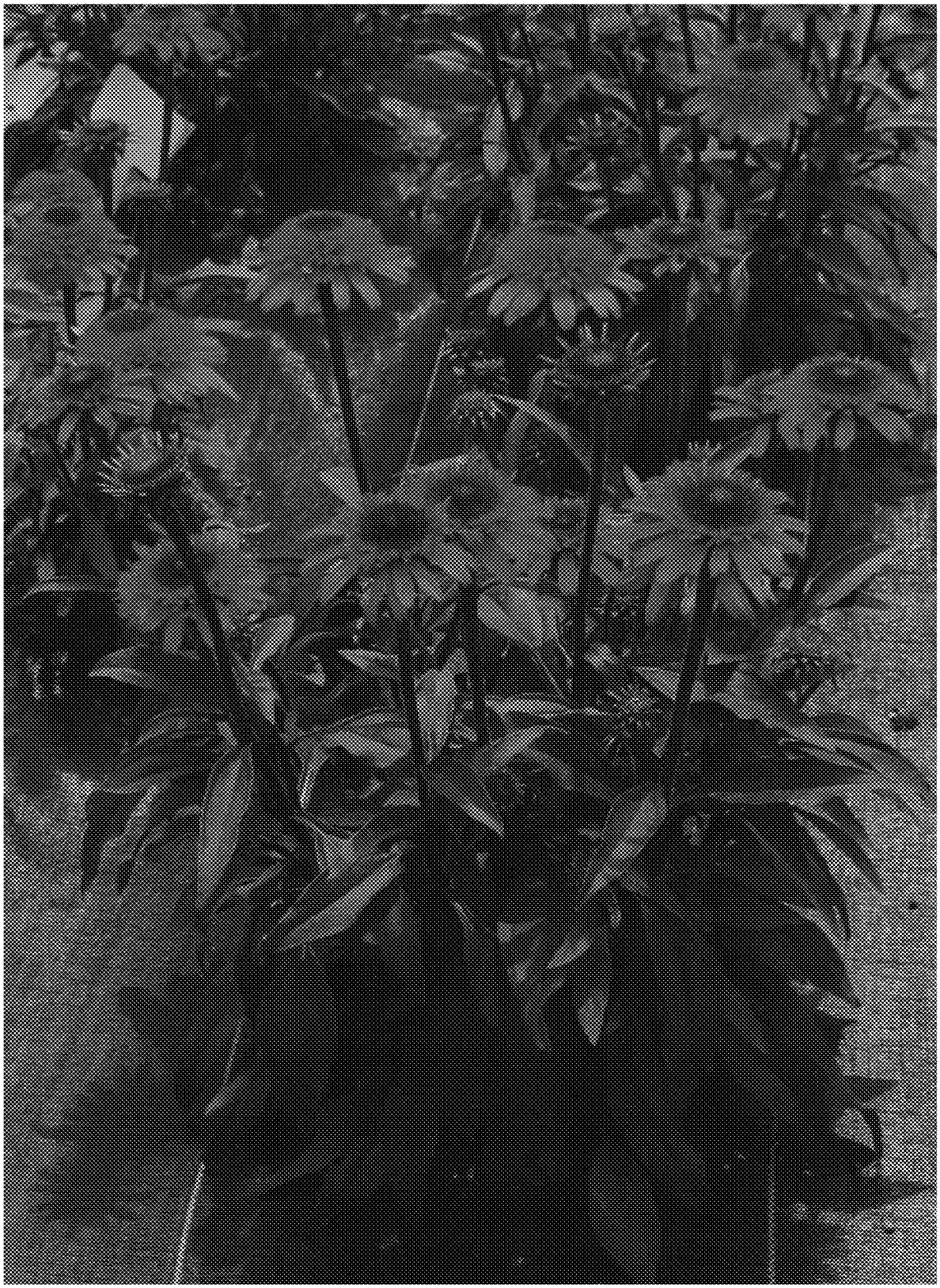
FIG. 2 shows a 7-month old plant of hie new variety growing in the trial field in full sunset in late July in Canby, Oreg.

The following detailed description sets forth the characteristics of the new variety based on observations of 17-month old plants growing in the trial bed in full sunset in Canby, Oreg. Canby is in Zone 8 on the USDA Hardiness map. Temperatures range from a high of 95° F. in August to an average of 32° F. in January. Normal rainfall is 42.8 inches per year in the trial fields in Canby, Oreg. Color references are primarily to The 2007 R.H.S. Colour Chart of The Royal Horticultural Society of London, 5$^{th}$ Edition.

PLANT

Type: Herbaceous perennial.

*Hardiness.*—USDA Zones 4 to 9.

*Size.*—38.0 cm wide and 40.0 cm tall to the top of inflorescences.

*Form.*—Basal clump, with about 19 stems from the base.

*Vigor.*—Excellent.

*Roots.*—Fibrous, with many downward growing and few laterals. Yellow-White Group RHS 158D in color. Roots develop easily from cuttings from the crown.

*Seeds.*—None observed.

*Fertility.*—None.

*Disease and pests.*—No pests or diseases have been observed on plants grown under commercial conditions in Canby. Oreg. No resistances are known.

*Stem* (*flowering*).—Type: Ascending, with 1 to 6 inflorescences per stem. Size: Up to 35.0 cm tall to a terminal inflorescence and 5.0 mm wide at the base. Strength: Excellent. Internode length: 2.0 to 5.0 cm. Surface texture: Strigose. Rugosity: Absent. Variegation: Absent. Color: Yellow-Green Group RHS 147B.

*Leaf* (*basal*).—Type: Simple. Shape: Lanceolate. Arrangement: Alternate, with about 15 leaves on the main stem. Blade size: Up to 14.0 cm long and 5.5 cm wide. Margins: Sparsely serrate to entire. Apex: Acuminate. Base: Attenuate. Surface texture: Strigose on both sides. Rugosity: Absent. Venation: Pinnate and Yellow-Green Group RHS 145A on both sides. Variegation: Absent. Color: The topside is Green Group RHS N137D and the bottom side is closest to Yellow-Green Group RHS 146A. Petiole description: Clasping, up to 3.0 cm long and 3.0 mm wide, scabrous, narrow leafy edges, and both sides are Yellow-Green Group RHS 148D.

*Leaf* (*stem*).—Type: Simple. Shape: Lanceolate. Arrangement: Alternate, with about 14 leaves on the main stem. Blade size: Up to 11.0 cm long and 2,2 cm wide. Margins: Sparsely serrate to entire. Apex: Acuminate. Base: Attenuate. Surface texture: Strigose on both sides. Rugosity: Absent. Venation: Pinnate and Yellow-Green Group RHS 147C on both sides. Variegation: Absent. Color: The topside is Green Group RHS N137C and the bottom side is closest to Green Group RHS 137B. Petiole description: Clasping, up to 4.0 cm long and 3.0 mm wide, scabrous, narrow leafy edges, and both sides are Yellow-Green Group RHS 145C.

INFLORESCENCE

Type: Composite, on terminal stalked heads.

*Flowering stem.*—24.0 cm tall from the base of the plant to the terminal leaves below the peduncle; branched, with 1 to 5 inflorescences per stem; diameter growing to 5.0 mm wide near the inflorescence; strigose; Yellow-Green Group RHS 145A and shaded with Greyed-Purple Group RHS 183A.

*Peduncle.*—13.0 cm long from above the terminal leaves to the flower; 3.0 cm wide; strigose; Yellow-Green Group RHS 146C.

*Size.*—Up to 6.0 cm wide and 5.0 cm deep as disc enlarges.

*Form.*—Ray florets are held slightly down, reflexing more in older inflorescences. The mature disc is rounded.

*Immature inflorescence* (*bud*).—2.3 cm wide and 2.0 cm deep; ray florets are held mostly upright and rolled up so only the back color of Orange Group RHS 25A shows; the disc color is Green Group RHS 143A.

*Ray florets.*—Ligulate; curvature is absent; without pistils or stamens; up to 17 in number; 42.0 mm long and 11.0 mm wide; ohianceolate with the tip being three-toothed (each acute); teeth cut 2.0 to 5.0 mm deep; florets with an entire margin; base attenuate; glabrous on both sides; horizontal to drooping attitude at origin; newly fully open florets having a topside of Greyed-Orange Group RHS 168 and a bottom side of Greyed-Orange Group RHS 169A; florets darken to Greyed-Orange Group RHS 169A near the base, blending to Orange-Red Group RHS 31A at the top, with a bottom side of Greyed-Orange Group RHS 169A.

*Disc.*—Anemone; flat becoming conic to 35.0 mm deep and 65.0 mm wide with maturity; overall color of Greyed-Orange Group RHS 169A.

*Disc florets.*—Curvature weakly reflexed; about 422 in number; mature flowers having 1 pistil and 4 stamens each; up to 20.0 mm long and 10.0 mm wide; each with one persistent, very stiff, linear bract (8.0 mm long, with 3.0 mm Greyed-Orange Group RHS 169A at apex blending to 3.0 mm Greyed-Orange Group RHS 169B to Greyed-Orange Group RHS 172A at base); showy 3 to 5-lobed corollas up to 22.0 mm long and 10.0 mm wide that are tubular on the bottom with the lobes spread out like a fan if 3-lobed (if 4 or 5-lobed, the extra lobes are linear segments) that are glabrous on both sides with a back side of Orange-Red Group RHS 31B and Orange-Red Group RHS N30B on the inside; pistil is 10.0 mm long; ovary is 3.5 mm long and White Group RHS NN155A; style is 5.0 mm long and White Group RHS 155A; 2-branched stigma spreading 2.0 mm wide and Yellow-Orange Group RHS 14B; stamen is 4.0 mm long and thread-like; anthers are 1.5 mm long and Grey-Brown Group RHS N199A; filaments are 2.5 mm long and White Group RHS 155A; no pollen present.

*Involucral bracts.*—In 4 leafy series with an area that grows to 32.0 mm wide and 12.0 mm deep; lobes are lanceolate in shape, reflexed, grow to 7.0 mm long and 3.0 mm wide, Green Group RHS N137C, margins strigose, tip acute, strigose on both sides.

*Receptacle.*—Up to 15.0 mm wide and 15.0 mm deep; White Group RHS NN155B.

*Bloom period.*—June through October in Canby, Oreg.

*Fragrance.*—Light.

*Lastingness.*—Each inflorescence lasts about two weeks on the plant in Canby, Oreg.

I claim:

1. A new and distinct variety of *Echinacea* plant named 'Moab Sunset', as is herein illustrated and described.

* * * * *